United States Patent [19] [11] 4,205,131
Almeida [45] May 27, 1980

[54] VIRUS PROPAGATION

[75] Inventor: June D. Almeida, London, England

[73] Assignee: Burroughs Wellcome Co., Research Triangle Park, N.C.

[21] Appl. No.: 965,045

[22] Filed: Nov. 30, 1978

[30] Foreign Application Priority Data

Dec. 1, 1977 [GB] United Kingdom ............... 50094/77
Dec. 24, 1977 [GB] United Kingdom ............... 53906/77

[51] Int. Cl.[2] ............................................. C12N 7/00
[52] U.S. Cl. ................................................... 435/235
[58] Field of Search ......................................... 195/1.1

[56] References Cited

PUBLICATIONS

Babiuk et al., Chem. Abst., vol. 88, (1978) 71141z.

*Primary Examiner*—Sam Rosen
*Attorney, Agent, or Firm*—Donald Brown

[57] ABSTRACT

A method of propagating rotavirus in vitro which comprises growing the virus in cell cultures susceptible to the virus in the presence of a serum-free medium containing a proteolytic enzyme. Such a method promotes the growth of virus in tissue culture, thus providing large quantities of antigen for immunization and for use in diagnostic tests.

7 Claims, No Drawings

VIRUS PROPAGATION

This invention relates to an improved method of propagating viruses in vitro so as to provide higher titres of virus particles, and in particular it relates to an improved method of propagating rotavirus in vitro.

It is well known that certain viruses are not easily cultured on an industrial scale, for example influenza virus will only grow to any appreciable titre in eggs. Bovine rotavirus is another example of a virus which will not grow easily in cell cultures; human rotavirus on the other hand will not multiply at all in cell cultures.

Rotavirus particles were first discovered in the stools of scouring calves as reported by Fernelius, A. L. et al in *Achiv fur die Gesamte Virusforschung,* 1972, 37, 114–130, and were designated rotavirus because of their wheel-like appearance under the electron microscope. Subsequently, it has been established that particles of identical morphology can be found in the faeces of other species, for example pigs, sheep and humans, and that they are invariably associated with gastroenteritis. Indeed, rotavirus is considered to be one of the chief causal agents in infantile gastroenteritis, particularly in the more underdeveloped countries.

At the present time, the main method, and in the case of human rotavirus the only satisfactory method, for obtaining whole virus particles in any quantity is to isolate the virus from faeces. Such isolation is usually accomplished by centrifugation, however it may also include filtration. Alternatively, in the case of bovine rotavirus the virus can be propagated on primary cell cultures; it is felt that the type of cells used should be species specific, that is for bovine virus primary calf cells, for example kidney cells, should be used. Until now it has been found impossible to grow human rotavirus on cell cultures. However, Banatvala, J. E. et al, (Lancet, Oct. 25, 1975, 821) have developed a specialised technique whereby the virus is centrifuged onto pig kidney cells. This method comprises growing the cell cultures on coverslips contained in flat-bottomed tubes, to which is added faecal filtrates, followed by centrifugation of the tube. This method results in the production of viral components, as demonstrated by fluorescent antibody, but not in the production of complete infectious virus.

The proteolytic enzyme trypsin has been reported to have several effects on cell cultures, and virus cultivation; Cunningham, D. and Ho, T. (Proteases and Biological Control, eds Reich et al, Cold Spring Harbor Laboratory, New York, 1975, 795–805) reported that trypsin stimulated the division of chick cells, if present for at least 2 hours. In 1965, Spendlove and Schaffer (J. Bact., 89, 597) showed that enzyme treatment enhanced infectivity of reovirus by cleaving the surface proteins of the virus.

It has now been found that by propagating virus, of the type which is not inactivated by the action of proteolytic enzymes, such as rotavirus, *in vitro,* in cell cultures in the presence of a serum-free medium containing a proteolytic enzyme, a greatly enhanced amount of virus is produced.

According to the present invention, therefore, there is provided a method of propagating rotavirus *in vitro,* comprising growing the virus in cell cultures susceptible to the virus in the presence of a serum-free medium containing a proteolytic enzyme.

The rotavirus, with which the cell culture is to be infected, can be prepared from any kind of clinical specimen known to be a source of the virus, for example it may be obtained from faecal material from such mammals as cattle, pigs, sheep, mice or humans. Such faecal material is for instance suspended in a suitable buffer, at a pH of between 5 and 9 so as to form a suspension of from 5 to 30% by weight, preferably about 20% by weight. The suspension is then clarified by centrifugation for up to 30 minutes at from 1000 to 10,000 g, preferably for 20 minutes at 5000 g. The supernatent left after centrifugation is processed firstly through a Millex (Millipore) filter having a pore size of from 150 to 0.45 μm, and then through a filter having a pore size of 0.22 μm. The resultant filtrate is found to be sufficiently clean for infecting tissue cultures.

Alternatively and more preferably the virus to be propagated may be a tissue culture adapted strain, that is, susceptible cells have been infected with the appropriate virus, and the virus subsequently serially passaged in such cultures. Such tissue culture adapted strains have the advantage that they are readily available without having to purify clinical specimens, and that they are likely to be attenuated, making them a better source for a potential vaccine. Furthermore such strains are likely to grow to a higher titre, thus providing greater quantities of virus.

One type of cell culture, for propagating the virus, comprises primary cells of the homologous species, so for example in the case of bovine rotavirus, primary calf kidney cells are used for propagation. However, a considerable technical advance is to employ established cell lines for the propagation of viruses; so far this has not been possible for rotavirus. Using the presently described method calf rotavirus can be propagated with advantage in the presence of trypsin on the human diploid MRC 5 cell line, the monkey kidney BSC-1 cell line, the monkey kidney LLC-MK2 cell line or Vero cells.

Once the cells selected for propagating the virus have become confluent, the serum containing medium in which the cells were growing must be removed, since serum and proteolytic enzymes are antagonists; the enzyme breaks down certain serum components. After washing the cells, a small amount of virus, present in a serum free maintenance medium, is added to the culture and allowed to adsorb for 15 to 60 minutes, preferably 30 minutes, at 35 to 39° C., preferably 37° C.

Following this, fresh maintenance medium for virus cultivation is added to the cell culture, which medium may be a chemically defined medium such as Eagles Minimal Essential Medium or Basal Medium, or Medium 199 (see Morgan, J. F., Morton, H. J. and Parker, R. C. (1950), Proc. Exp. Biol. (N.Y.), 73, 1). For the purposes of the present invention such media are not supplemented with the usual quantity of serum, but may optionally contain antibiotics, to control contamination, or other non-proteinaceous additives.

However the maintenance medium used for adsorption and maintenance, according to the present invention is supplemented with a proteolytic enzyme such as trypsin chymotrypsin, pancreatin, pronase, bromelain or subtilisin, which may conveniently be incorporated into the medium in a concentration from 1.0 μg/ml to 20 μg/ml, preferably 2.0 μg/ml to 10 μg/ml. The culture is then incubated at from 35° to 39° C., preferably 37° C. for from about 1 to 3 days, preferably 2 days, after which time the cells have detached from the support.

Examination of virus infected cells in the electron microscope shows that with viruses that will not grow in tissue culture, virus growth has occurred, and with those that grow only poorly in cells, increased titres of virus have been produced.

The main advantage of this propagation method is that it promotes the growth of rotavirus in tissue culture which previously would not grow or was difficult to grow in such systems, and also provides large quantities of virus to be produced in cells where hitherto only small quantities have grown. Large amounts of antigen will therefore become available for immunisation and for use in diagnostic tests such as immune electron microscopy, immunodiffusion, haemagglutination, complement fixation, ELISA and radio-immunoassay. By producing hitherto unobtainable large quantities of rotavirus, it may be possible to manufacture a viral vaccine for administration to mammals. Rotavirus gastroenteritis causes the deaths of young animals in considerable numbers and therefore development of a vaccine against this disease is of great economic importance. In addition by this method it should be possible to produce virus in a quantity and purity suitable for a vaccine for administration to humans, thus helping to reduce the numerous infantile deaths due to rotavirus gastroenteritis.

Further advantages of the present invention will become apparent from the following description of the embodiments of the invention, which embodiments, however, do not limit this invention in any way.

EXAMPLE 1

Several bottles (150 ml) of confluent cultures of primary calf kidney cells were washed three times with phosphate buffered saline (PBS) without calcium, but containing 5000 International Standard Units penicillin and 2500 International Standard Units streptomycin. The cultures were finally drained and 1 ml of calf rotavirus having been adapted to tissue culture (i.e. at its 6th pass in primary calf kidney cells) and contained in serum free maintenance medium was added, and allowed to adsorb for ½ hour at 37° C. After this time serum free maintenance medium was added to the cultures, the medium comprised Eagles basal medium containing 5000 International Standard Units penicillin and 2500 International Standard Units streptomycin and a final concentration of 0.1% sodium bicarbonate. The medium in the first bottle contained 1 μg of trypsin, the second contained 5 μg of trypsin and the third contained 10 μg of trypsin, 1 μg, 5 μg or 10 μg/ml of crystalline trypsin made up in $10^{-3}$ M hydrochloric acid. In addition control cultures were set up, one set comprised infected cells grown in the absence of trypsin, and a second set comprising uninfected cells grown in the presence of trypsin. All cultures were incubated at 37° C. and examined at regular intervals for the appearance of cytopathic effect (CPE).

At 48 hours the appearance of the cells was as shown in the table where + = 25% CPE and ++++ = 100% CPE.

| Amount of trypsin | Cytopathic effect in uninfected cells | Cytopathic effect in infected cells |
|---|---|---|
| No trypsin | — | — |
| 1 μgm | + | + |
| 5 μgm | ++++ | ++++ |
| 10 μgm | ++++ | ++++ |

In spite of the fact that the control cells with the higher amounts of trypsin had not survived, all the virus infected cultures were examined in the electron microscope. This was done by removing any remaining cells from the plastic support and harvesting cells plus supernatant. Aliquots of the virus cultures (5 ml) were then centrifuged for 1 hr at 10,000 g and the pellet so obtained used for negative staining. Assessment of the preparations so obtained in the electron microscope was as follows.

| Amount of Trypsin in virus culture | Amount of Virus present |
|---|---|
| No trypsin | Approx $10^6$ particles/ml |
| 1 μg | Approx $10^7$ particles/ml |
| 5 μg | Approx $10^8$ particles/ml |
| 10 μg | Approx $10^9$ particles/ml |

It would therefore appear that, in spite of the amount of trypsin at the higher levels being lethal to the cells, a greatly enhanced amount of virus has been obtained with this procedure.

EXAMPLE 2

Serial Passage of Rotavirus in MRC-5 Cell Line

Passage 1

MRC-5 human diploid tissue culture cells were cultured in 75 ml Corning flasks in a growth medium comprising Eagles Basal Medium containing 5000 International Standard Units (ISU) of penicillin, 2500 ISU, 0.1% sodium bicarbonate and 10% foetal calf serum, for 3 days after which time they were confluent. The growth medium was removed and the confluent cultures washed three times in PBS containing 5000 ISU of penicillin and 2500 ISU of streptomycin. The cultures were finally drained and 1 ml of tissue culture adapted calf rotavirus (at 6th pass in primary calf kidney cells) was added and the virus allowed to adsorb for 1 hour at 37° C. After this the cultures were overlaid with serum-free medium (40 ml) comprising Eagles Basal Medium containing 5000 ISU of penicillin, 2500 ISU of streptomycin, 0.2% sodium bicarbonate plus 10 μg/ml of crystalline trypsin made up in $10^{-3}$M hydrochloric acid, and incubated for 48–72 hours at 37° C.

After 24 hours the cells were completely detached from the flask surface.

Passage 2

The suspension from passage 1 was harvested after 48–72 hours and used as the inoculum for a second passage through MRC-5 cells following the method for passage 1.

Passage 3

The cell harvest from passage 2 was used as the inoculum for a third passage through MRC-5 cells, following the method for passage 1.

Electron microscopy by negative staining showed high titres of rotavirus at all passage levels.

EXAMPLE 3

Culturing of Rotavirus in BSC-1 Cell Line (ATCC CCL 26)

BSC—1 monkey kidney tissue culture cells were cultured in 75ml Corning flasks in a growth medium comprising Eagles Basal Medium containing 5000 International Standard Units (ISU) of penicillin, 2500 ISU, 0.1% sodium bicarbonate and 10% foetal calf serum, for 3 days after which time they were confluent. The growth medium was removed and the confluent cultures washed three times in PBS containing 5000 ISU of penicillin and 2500 ISU of streptomycin. The cultures were finally drained and 1 ml of tissue culture adapted calf rotavirus (at 6th pass in primary calf kidney cells) was added and the virus allowed to adsorb for 1 hour at 37° C. After this the cultures were overlaid with serum-fee medium (40 ml) comprising Eagles Basal Medium containing 5000 ISU of penicillin, 2500 ISU of streptomycin, 0.2% sodium bicarbonate plus 10 $\mu$g/ml of crystalline trypsin made up in $10^{-3}$M hydrochloric acid, and incubated for 48–72 hours at 37° C.

After 24 hours the cells were completely detached from the flask surface. Electron microscopy by negative staining showed high titres of rotavirus.

EXAMPLE 4

The procedure used in example 3 was followed except that LLC - MK2 (ATCC CCL 7) monkey kidney cells were substituted for the BSC -1 cells, with the result that high titres of rotavirus were produced.

EXAMPLE 5

The procedure used in example 3 was followed except that Vero cells (ATCC CCL 81) were substituted for the BSC -1 cells, will the resultant production of high titres of rotavirus.

I claim:

1. A method of propagating rotavirus in vitro comprising growing the virus in cell cultures susceptible to the virus in the presence of a serum-free medium containing a proteolytic enzyme.

2. A method as claimed in claim 1 wherein the cell cultures susceptible to rotavirus comprise primary calf kidney cells, human diploid MRC 5 cells, monkey kidney BSC-1 cells, monkey kidney LLC - MK2 cells or Vero cells.

3. A method as claimed in claim 1 or claim 2 wherein the serum-free medium is a chemically defined maintenance medium.

4. The method of claim 3 wherein the proteolytic enzyme is trypsin, chymotrypsin, pancreatin, pronase, bromelain or subtilisin.

5. The method of claim 4 wherein the enzyme is present in the medium in a concentration from 1.0 $\mu$g/ml to 20 $\mu$g/ml.

6. The method of claim 5 wherein the cell cultures infected with virus are incubated at from 35° to 39° C.

7. A method as claimed in claim 6 wherein the infected cell cultures are incubated for from 1 to 3 days.

* * * * *